United States Patent
Connor et al.

[11] 4,046,769
[45] Sept. 6, 1977

[54] 4,10-DIHYDRO-4,10-DIOXO-1H-1-BENZOPYRANO[3,2-B]PYRIDINE-2-CARBOXYLIC ACIDS AND ESTERS

[75] Inventors: David T. Connor, Parsippany; Patricia A. Young, Madison; Max von Strandtmann, Rockaway, all of N.J.

[73] Assignee: Warner-Lambert Company, Morris Plains, N.J.

[21] Appl. No.: 736,788

[22] Filed: Oct. 29, 1976

[51] Int. Cl.² .................................. C07D 491/04
[52] U.S. Cl. .......................... 260/295 T; 424/263; 260/345.2
[58] Field of Search .............................. 260/295 T

[56] References Cited
U.S. PATENT DOCUMENTS

| | | | |
|---|---|---|---|
| 3,689,497 | 9/1972 | Brown et al. | 260/295 T |
| 3,706,764 | 12/1972 | Oita et al. | 260/327 TH |

Primary Examiner—Lorraine A. Weinberger
Assistant Examiner—Lisa Jones
Attorney, Agent, or Firm—Albert H. Graddis; Frank S. Chow

[57] ABSTRACT

There is disclosed 4,10-dihydro-4,10-dioxo-1H-1-benzopyrano[3,2-b]pyridine-2-carboxylic acids, salts and esters of the formula:

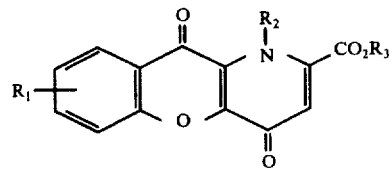

wherein $R_1$ is hydrogen, lower alkyl, halogen, hydroxy or lower alkoxy; $R_2$ is hydrogen, aralkyl or lower alkyl; $R_3$ is hydrogen or lower alkyl and their pharmaceutically acceptable salts.

These compounds are useful in the management of allergic conditions such as bronchial asthma, hay fever and so on.

14 Claims, No Drawings

4,10-DIHYDRO-4,10-DIOXO-1H-1-BENZOPYRANO[3,2-b]PYRIDINE-2-CARBOXYLIC ACIDS AND ESTERS

The present invention relates to 4,10-dihydro-4,10-dioxo-1H-1-benzopyrano[3,2-b]pyridine-2-carboxylic acids, salts and esters having the following structural formula:

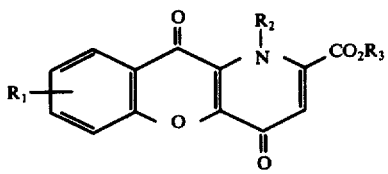

I.

wherein $R_1$ is hydrogen, lower alkyl, halogen, hydroxy or lower alkoxy; $R_2$ is hydrogen, aralkyl or lower alkyl; $R_3$ is hydrogen or lower alkyl and their pharmaceutically acceptable salts.

In the above definitions for $R_1$, $R_2$ and $R_3$, lower alkyl and the lower alkyl portions of lower alkoxy and aralkyl are meant to have 1-6 carbon atoms. These include, for example, methyl, ethyl, propyl, isopropyl, butyl, isobutyl and so on. The term "halogen" includes all of its four members, i.e., chlorine, bromine, fluorine and iodine. The aryl portion is meant to denote a monocyclic aromatic hydrocarbon having 6-10 carbon atoms, e.g., phenyl, tolyl and the like.

Embraced within the scope of the present invention are the pharmaceutical compositions comprising the aforesaid compounds or their salts in association with a pharmacologically inert carrier. Also included within the scope of the present invention are methods for the management of allergic conditions by the administration of said pharmaceutical compositions.

The compounds of the present invention, including their salts, have been found to inhibit and prevent allergic and asthmatic reactions. For example, at a dose of 0.5 mg/kg to 100 mg/kg intravenously, Compounds I or their salts were found to prevent allergic and asthmatic reactions in the passive cutaneous anaphylaxis (PCA) screen. This PCA screen is a modification of procedures described by I. Mota, Life Sciences, 7: 465 (1963) and Z. Ovary and O. Bier, Proc. Soc. Exptl. Biol. Med., 81: 585 (1952). The compound 8-chloro-4,10-dihydro-4,10-dioxo-1H-1-benzopyrano[3,2-b]-pyridine-2-carboxylic acid is particularly preferred because at a dose of 0.5 mg/kg, the PCA screen shows a 43 percent inhibition of the allergic reactions.

In view of the above biological activity, the compounds of this invention, including their salts, are indicated in the management of patients with allergic manifestations such as bronchial asthma and hay fever. Generally speaking, a dose of 0.5 mg/kg to 100 mg/kg orally, parenterally or by inhalation one to three times daily is suggested. As with any anti-allergic therapy, the dosage regimen must be titrated to individual needs by methods well-known to the healing arts.

In order to use these compounds and their salts, they are to be formulated into conventional dosage forms such as tablets, elixers and aerosols by known pharmaceutical technology. For example, tablets can be prepared by selecting the active ingredient, mixing with lactose and compressed into tablets with suitable tabletting excipients known in the art.

The above Compounds I are prepared in accordance with the following reaction scheme:

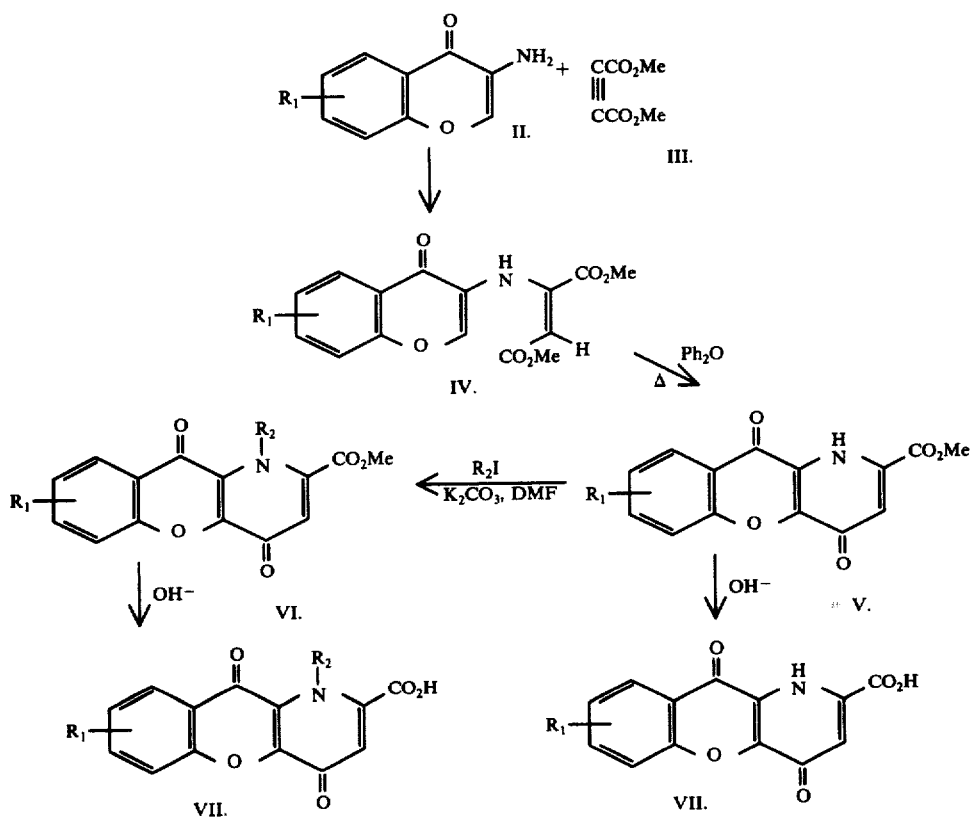

Referring to the above reaction scheme, Compound II is treated with Compound III in an alcoholic solvent, e.g., methanol, to obtain Compound IV. The treatment of Compound IV with diphenyl ether at reflux results in the production of Compound V. Compound V, when treated with $R_2$ iodide, in the presence of potassium carbonate and dimethyl formamide under an atmosphere of nitrogen, results in the production of those compounds of the invention in which $R_3$ is methyl. Hydrolysis of Compound VI results in those compounds of the invention in which $R_3$ is hydrogen.

Similarly, hydrolysis of Compound V results in the production of the compounds of this invention in which $R_2$ and $R_3$ are hydrogen. Salts of the carboxylic acids of this invention are produced by treating the acids with bases such as sodium carbonate, potassium carbonate and calcium carbonate, and the like.

The salts of Compound I are prepared by treating the parent base with an acid, for example, a mineral acid such as hydrochloric, sulfuric, nitric and phosphoric in stoichiometric amounts and recovering the salt produced by conventional procedures.

The starting materials were prepared as follows:

3-Aminochromone by the method of G. J. P. Beckett and G. P. Ellis, *Tetrahedron Letters*, 719 (1976); 3-amino-6-chlorochromone and 3-amino-7-methoxychromone by the methods described in our co-pending application Ser. No. 736,926, Oct. 29, 1976, filed concurrently herewith, entitled "4,10-Dihydro-4,10-dioxo-1H-1-benzopyrano[3,2-b]pyridine-3-carboxylic acid". The disclosure of this application is incorporated herein by reference. Dimethyl acetylenedicarboxylate is available from Aldrich Chemical Company.

To further illustrate the practice of this invention, the following examples are included. Temperatures hereinafter are in degrees Centigrade.

EXAMPLE 1

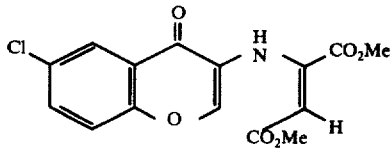

Dimethyl 2-[(6-chloro-4-oxo-4H-1-benzopyran-3-yl)amino]-2-butenedioate

A mixture of 3-amino-6-chlorochromone (8 g, 0.041 mole) and dimethyl acetylenedicarboxylate (10.5 g, 0.074 mole) in methanol (150 ml) was stirred at room temperature for 2 days. The product was filtered off and washed with methanol. Recrystallization from ethyl acetate gave yellow crystals (11 g, 80%), m.p. 158°–160°.

Anal. Calcd. for $C_{15}H_{12}ClNO_6$: C, 53.35; H, 3.58; N, 4.15; Cl, 10.50. Found: C, 53.31; H, 3.68; N, 4.13; Cl, 10.64.

NMR (CDCl$_3$) δ 9.45 (bs, 1, N-H, exchanges with D$_2$O), 8.4 to 7.4 (m, 4, ArH), 5.62 (s, 1, vinyl) and 3.75 (s, 6, OMe).

IR 3300, 3200 (N-H), 1750 (CO), 1680 (CO) and 1650 (CO).

UV 317 (18,000).

EXAMPLE 2

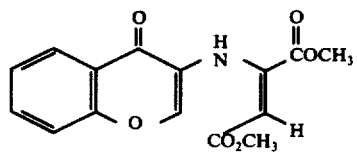

Dimethyl 2-[4-oxo-4H-1-benzopyran-3-yl)amino]-2-butenedioate

A mixture of 3-aminochromone (8.0 g, 0.05 mole) and dimethyl acetylenedicarboxylate (12.8 g, 0.09 mole) in methanol (200 ml) was stirred at room temperature for 2.5 hrs. The product was filtered off and washed with ethyl acetate. Recrystallization from absolute ethanol gave white crystals (8.75 g, 58%), m.p. 155°–157°.

Anal. Calcd. for $C_{15}H_{13}NO_6$: C, 59.40; H, 4.32; N, 4.62. Found: C, 59.21; H, 4.43; N, 4.87.

NMR (CDCl$_3$) δ 9.43 (bs, 1, NH, exchanges with D$_2$O), 7.94 (s, 1, C$_2$H), 8.2 (md, 1, ArH), 7.47 (m, 3, ArH), 5.62 (s, 1, CH), 3.75 (s, 6, CH$_3$).

IR 3240 (NH), 1738 (CO), 1668 (CO).

UV 238 (16,540), 314 (18,440).

EXAMPLE 3

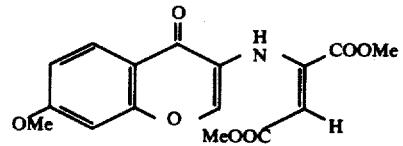

Dimethyl 2-[(7-methoxy-4-oxo-4H-1-benzopyran-3-yl)amino]-2-butenedioate

Prepared by the procedure described for Ex. 1 from 3-amino-7-methoxy-4H-1-benzopyran-4-one (4.4 g, 0.023 mole). The crystals were yellow (2.95 g, 38.2%), m.p. 134°–138° C.

Anal. Calcd. for $C_{16}H_{15}NO_7$: C, 57.66; H, 4.54; N, 4.20. Found: C, 56.39; H, 4.41; N, 4.16.

NMR (CDCl$_3$) δ 9.4 (bs, 1, NH, exchanges with D$_2$O), 8.11 (d, 1, C$_5$H), 7.85 (s, 1, C$_2$H), 6.92 (md, 2, C$_6$H and C$_8$H), 5.59 (s, 1, CH), 3.90 (s, 3, OCH$_3$), 3.78 (s, 6, OCH$_3$ and ArOCH$_3$).

M.S. Molecular ion 333 M$^+$

EXAMPLE 4

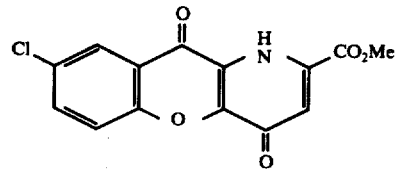

Methyl 8-chloro-4,10-dihydro-4,10-dioxo-1H-1-benzopyrano[3,2-b]pyridine-2-carboxylate Dimethyl 2-[(6-chloro-4-oxo-4H-1-benzopyran-3-yl)amino]-2-butenedioate (1.0 g, 0.0033 mole) was added to diphenyl ether (25 ml) at 200°. The reaction mixture was refluxed for 10 min. (bath temperature 260°–280°). The product, which crystallized out on cooling, was filtered off and washed with ether. Recrystallization from DMF gave white crystals (0.8 g, 88%), m.p. 300°–305°.

Anal. Calcd. for C₁₄H₈ClNO₅: C, 55.01; H, 2.64; N, 4.58; Cl, 11.60. Found: C, 54.92; H, 2.74; N, 4.44; Cl, 11.56.

NMR (TFA) δ 8.6 to 7.8 (m, 4, ArH) and 4.30 (s, 3, OMe).

IR 3300 (N-H), 1750 (CO).

UV 251 (51,000), 350 (10,000), 365 (10,000).

EXAMPLE 5

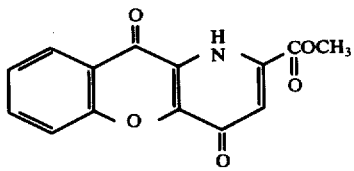

Methyl 4,10-dihydro-4,10-dioxo-1H-1-benzopyrano[3,2-b]pyridine-2-carboxylate

Prepared by the method described for Ex. 4 from dimethyl 2-[(4-oxo-4H-1-benzopyran-3-yl)amino]-2-butenedioate (20.0 g, 0.66 mole). Recrystallization from DMF gave white crystals (5.0 g, 36.5%), m.p. 244°–245° C.

Anal. Calcd. for C₁₄H₉NO₅: C, 61.99; H, 3.34; N, 5.16. Found: C, 61.73; H, 3.36; N, 5.11.

NMR (TFA) δ 8.5 (md, 1, ArH), 8.28 (s, 1, C₃H), 7.96 (m, 3, ArH), 4.31 (s, 3, CH₃).

IR 3290 (NH), 1742 (CO), 1677 (CO), 1638 (CO).

UV 242 (32,000), 260 (23,500), 360 (7,100).

EXAMPLE 6

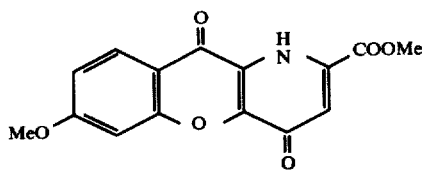

Methyl 7-methoxy-4,10-dihydro-4,10-dioxo-1H-1-benzopyrano[3,2-b]pyridine-2-carboxylate Prepared by the method described for Ex. 4 from dimethyl 2-[(7-methoxy-4-oxo-4H-1-benzopyran-3-yl)amino]-2-butenedioate (2.6 g, 0.0077 mole). Recrystallization from DMF gave light brown crystals, (0.9 g, 38.6%), m.p. 258°–260° C.

Anal. Calcd. for C₁₅H₁₁NO₆: C, 59.80; H, 3.68; N, 4.65. Found: C, 59.65; H, 3.73; N, 4.75.

NMR (TFA) δ 8.58 (d, 1, C₉H), 8.30 (s, 1, C₃H), 7.40 (m, 2, C₆H and C₈H), 4.38 (s, 3, OCH₃), 4.19 (s, 3, OCH₃).

IR 3360 (NH), 1735 (CO), 1622 (CO).

UV 242 (26,850), 277 (15,650), 313 (11,700).

EXAMPLE 7

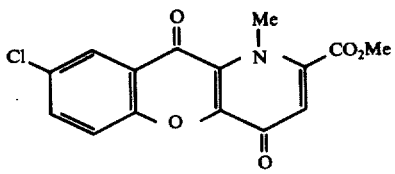

Methyl 1-methyl-8-chloro-4,10-dihydro-4,10-dioxo-1H-1-benzopyrano[3,2-b]-pyridine-2-carboxylate A mixture of methyl 8-chloro-4,10-dihydro-4,10dioxo-1H-1-benzopyrano-[3,2-b]pyridine-2-carboxylate (7.0 g, 0.023 mole), methyl iodide (14 g, 0.099 mole) and potassium carbonate (3.22 g, 0.023 mole) in dimethyl formamide (100 ml) was stirred at 100° under nitrogen for 3 hrs. The reaction mixture was cooled. The product, which precipitated, was filtered, washed with water and dried. Recrystallization from DMF gave white crystals (6.3 g, 86%), m.p. 276°–278°.

Anal. Calcd. for C₁₅H₁₀ClNO₅: C, 56.35; H, 3.15; N, 4.38; Cl, 11.09. Found: C, 56.13; H, 3.23; N, 4.27; Cl, 11.28.

NMR (TFA) δ 8.70 to 7.70 (m, 3, ArH), 8.48 (s, 1, C₃H), 4.67 (s, 3, NCH₃) and 4.40 (s, 3, OCH₃).

IR 1720 (CO), 1675 (CO).

UV 250 (42,000), 340 (6,000).

EXAMPLE 8

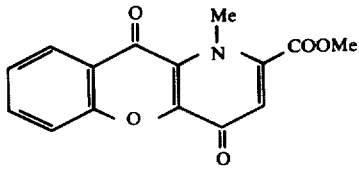

Methyl 1-methyl-4,10-dihydro-4,10-dioxo-1H-1-benzopyrano[3,2-b]pyridine-2-carboxylate Prepared by the method described for Ex. 7 from methyl 4,10-dihydro-4,10-dioxo-1H-1-benzopyrano[3,2-b]pyridine-2-carboxylate (W14,178) (3.0 g, 0.011 mole). Recrystallization from DMF gave white crystals (2.15 g, 68.4%), m.p. 290°–293° C.

Anal. Calcd. for C₁₅H₁₁NO₅: C, 63.16; H, 3.89; N, 4.91. Found: C, 62.92; H, 3.91; N, 4.85.

NMR (TFA) δ 7.7 – 8.8 (m, 4, ArH), 8.51 (s, 1, C₃H), 4.70 (s, 3, NCH₃), 4.40 (s, 3, OCH₃).

IR 1715 (CO), 1678 (CO).

UV 247 (36,700), 332 (6,400).

EXAMPLE 9

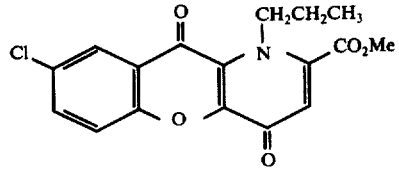

Methyl 1-propyl-8-chloro-4,10-dihydro-4,10-dioxo-1H-1-benzopyrano[3,2-b]-pyridine-2-carboxylate Prepared from methyl 8-chloro-4,10-dihydro-4,10-dioxo-1H-1-benzopyrano-[3,2-b]pyridine-2-carboxylate (4.5 g, 0.015 mole) and n-propyl iodide (9.1 g, 0.054 mole) by the method described for Ex. 7. Recrystallization from methanol gave white crystals (1.77 g, 35%), m.p. 240°-244°.

Anal. Calcd. for $C_{17}H_{14}ClNO_5$: C, 58.72; H, 4.06; N, 4.03; Cl, 10.20. Found: C, 58.92; H, 4.28; N, 3.86; Cl, 10.34.

NMR (TFA) δ 8.70 to 7.70 (m, 3, ArH), 8.51 (s, 1, $C_3H$), 4.90 (t, 2, $CH_2N$), 4.40 (s, 3, $OCH_3$), 2.35 (m, 2, $CH_2$) and 1.42 (t, 3, $CH_3$).

IR 1725 (CO), 1675 (CO).
UV 249 (44,000), 346 (6,000).

EXAMPLE 10

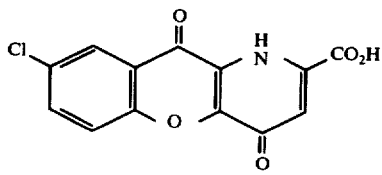

8-Chloro-4,10-dihydro-4,10-dioxo-1H-1-benzopyrano[3,2-b]pyridine-2-carboxylic acid A suspension of methyl 8-chloro-4,10-dihydro-4,10-dioxo-1H-1-benzopyrano[3,2-b]pyridine-2-carboxylate (1 g, 0.0034 mole) in 1N sodium hydroxide solution (20 ml) was stirred at room temperature for 24 hrs. The solid was filtered off, washed with water, with acetone, and suspended in 5N hydrochloric acid. The product was filtered off, washed with water, with acetone, and sucked dry. Recrystallization from DMF gave white crystals (0.775 g, 81%), m.p. 290°-320° (dec.).

Anal. Calcd. for $C_{13}H_6NO_5Cl$: C, 53.54; H, 2.07; N, 4.80; Cl, 12.16. Found: C, 53.26; H, 2.22; N, 4.76; Cl, 12.10.

NMR (TFA) δ 8.6 to 7.8 (m, 4, ArH).
IR 3320 (NH), 2700 - 2400 (OH), 1700 (CO), 1650 (CO).
UV 250 (37,000), 261 (32,000), 362 (10,000).

EXAMPLE 11

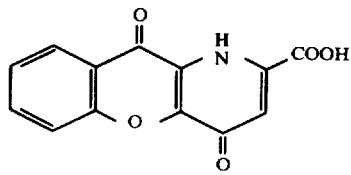

4,10-Dihydro-4,10-dioxo-1H-1-benzopyrano[3,2-b]pyridine-2-carboxylic acid

Prepared by the method described for Ex. 10 from methyl 4,10-dihydro-4,10-dioxo-1H-1-benzopyrano[3,2-b]pyridine-2-carboxylate (9.8 g, 0.0372 mole). Recrystallization from DMF gave off-white crystals (6.7 g, 72.2%), m.p. chars > 290° C.

Anal. Calcd. for $C_{13}H_7NO_5$: C, 60.71; H, 2.74; N, 5.45. Found: C, 60.60; H, 3.01; N, 5.74.

NMR (TFA) δ 8.8 - 7.6 (m, 4, ArH), 8.32 (s, 1, $C_3H$).
IR 3330 (NH), 1730 (CO), 1658 (CO), 1608 (CO).
UV 244 (30,800), 257 (26,000), 357 (10,000).

EXAMPLE 12

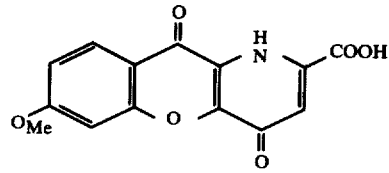

7-Methoxy-4,10-dihydro-4,10-dioxo-1H-1-benzopyrano[3,2-b]pyridine-2-carboxylic acid Prepared by the method described for Ex. 10 from methyl 7-methoxy-4,10-dihydro-4,10-dioxo-1H-1-benzopyrano[3,2-b]pyridine-2-carboxylate (0.70 g, 0.00232 mole). Recrystallization from DMF gave off-white crystals (0.28 g, 42%), m.p. 253°-254°.

Anal. Calcd. for $C_{14}H_9NO_6$: C, 58.54; H, 3.16; N, 4.88. Found: C, 58.89; H, 3.59; N, 5.27.

NMR (TFA) δ 8.48 (d, 1, $C_9H$), 8.38 (s, 1, $C_3H$), 7.41 (m, 2, $C_6H$ and $C_8H$), 4.20 (s, 3, $OCH_3$).
IR 3370 (NH), 2800 - 2300 (COOH), 1733 (CO), 1673 (CO).
UV (Qualitative) $\lambda_{max}$ 216, 242, 274, 320.
MS Decarboxylated in Mass Spectrometer
Observed ($M^+ - 44$): 243.0495
Calculated for $C_{13}H_9NO_4$: 243.0532

EXAMPLE 13

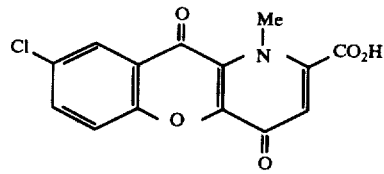

1-Methyl-8-chloro-4,10-dihydro-4,10-dioxo-1H-1-benzopyrano[3,2-b]pyridine-2-carboxylic acid Prepared by the method described for Ex. 10 from methyl 1-methyl-8-chloro-4,10-dihydro-4,10-dioxo-1H-1-benzopyrano[3,2-b]pyridine-2-carboxylate (1.0 g, 0.003 mole). Recrystallization from DMF gave white crystals (0.81 g, 85%), m.p. 241°-242°.

Anal. Calcd. for $C_{14}H_8ClNO_5$: C, 55.01; H, 2.64; N, 4.58; Cl, 11.60. Found: C, 54.67; H, 2.76; N, 4.38; Cl, 11.69.

NMR (TFA) δ 8.80 - 7.80 (m, 3, ArH), 8.59 (s, 1, $C_3H$), 4.75 (s, 3, $CH_3$).
IR 3320 (OH), 1725 (CO) and 1675 (CO).
UV 250 (45,000), 346 (6,000).

EXAMPLE 14

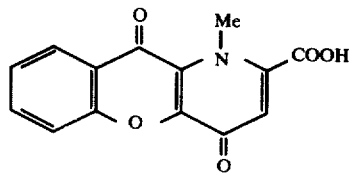

1-Methyl-4,10-dihydro-4,10-dioxo-1H-1-benzopyrano[3,2-b]pyridine-2-carboxylic acid Prepared by the procedure described for Ex. 10 from methyl 1-methyl-4,10-dihydro-4,10-dioxo-1H-1-benzopyrano[3,2-b]pyridine-2-carboxylate (2.0 g, 0.00702 mole). Recrystallization from DMF gave white crystals (1.63 g, 86%), m.p. 220° C.

Anal. Calcd. for $C_{14}H_9NO_5$: C, 61.99; H, 3.34; N, 5.16. Found: C, 61.85; H, 3.34; N, 5.16.

NMR (TFA) δ 8.62 (d), 7.6 – 8.5 (m) (4, ArH), 8.57 (s, 1, $C_3H$), 4.73 (s, 3, $CH_3$).

IR 3420 (OH), 3290 (OH), 3110 (OH), 1762 (CO), 1672 (CO).

UV 247 (38,920), 334 (6,360).

EXAMPLE 15

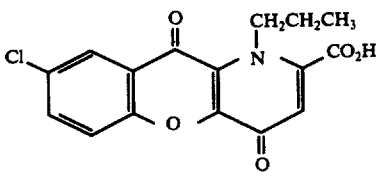

1-n-Propyl-8-chloro-4,10-dihydro-4,10-dioxo-1H-1-benzopyrano[3,2-b]pyridine-2-carboxylic acid Prepared by the method described for Ex. 10 from methyl 1-n-propyl-8-chloro-4,10-dihydro-4,10-dioxo-1H-1-benzopyrano[3,2-b]pyridine-2-carboxylate (1.4 g, 0.004 mole). Recrystallization from DMF gave white crystals (1.15 g, 86%), m.p. 224°–225°.

Anal Calcd. for $C_{16}H_{12}ClNO_5$: C, 57.59; H, 3.62; N, 4.20; Cl, 10.62. Found: C, 57.34; H, 3.73; N, 4.01; Cl, 10.81.

MNR (TFA) δ 8.70 – 7.70 (m, 3, ArH), 8.51 (s, 1, $C_3H$), 4.90 (t, 2, $CH_2N$), 2.35 (m, 2, $CH_2$) and 1.42 (t, 3, $CH_3$).

IR 3450, 3275, 3190, 1767, 1680.

UV 249 (45,500), 346 (6,000).

EXAMPLE 16

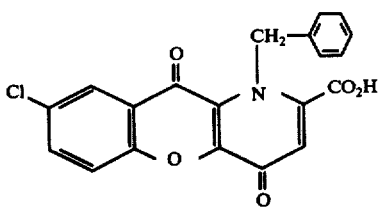

1-Benzyl-8-chloro-4,10-dihydro-4,10-dioxo-1H-1-benzopyrano[3,2-b]pyridine-2-carboxylic acid A mixture of methyl 8-chloro-4,10-dihydro-4,10-dioxo-1H-1-benzopyrano-[3,2-b]pyridine-2-carboxylate (2.0 g, 0.0065 mole), benzyl bromide (5.0 g, 0.029 mole) and potassium carbonate (2.0 g) in dimethyl formamide (100 ml) was stirred at 140° under nitrogen for 7 hrs. The reaction mixture was cooled and poured into water (500 ml). The aqueous solution was decanted from the product, which settled as an oil on the bottom of the flask. The oil crystallized from acetone and was recrystallized from DMF to give white crystals (1.2 g, 48%), m.p. 269°–271°.

Anal. Calcd. for $C_{20}H_{12}ClNO_5$: C, 62.90; H, 3.14; N, 3.66; Cl, 9.30. Found: C, 62.34; H, 3.19; N, 3.59; Cl, 9.99.

Mass Spectrum shows molecular ion at 381 for $C_{20}H_{12}ClNO_5$.

We claim:

1. A compound of the formula:

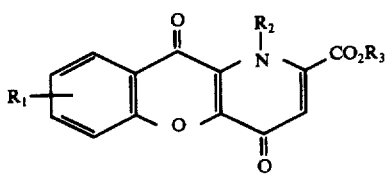

wherein $R_1$ is hydrogen, lower alkyl, halogen, hydroxy or lower alkoxy; $R_2$ is hydrogen, aralkyl or lower alkyl; $R_3$ is hydrogen or lower alkyl.

2. A compound according to claim 1 which is methyl 8-chloro-4,10-dihydro-4,10-dioxo-1H-1-benzopyrano[3,2-b]pyridine-2-carboxylate.

3. A compound according to claim 1 which is methyl 4,10-dihydro-4,10-dioxo-1H-1-benzopyrano[3,2-b]pyridine-2-carboxylate.

4. A compound according to claim 1 which is methyl 7-methoxy-4,10-dihydro-4,10-dioxo-1H-1-benzopyrano[3,2-b]pyridine-2-carboxylate.

5. A compound according to claim 1 which is methyl 1-methyl-8-chloro-4,10-dihydro-4,10-dioxo-1H-1-benzopyrano[3,2-b]-pyridine-2-carboxylate.

6. A compound according to claim 1 which is methyl 1-methyl-4,10-dihydro-4,10-dioxo-1H-1-benzopyrano[3,2-b]pyridine-2-carboxylate.

7. A compound according to claim 1 which is methyl 1-propyl-8-chloro-4,10-dioxo-1H-1-benzopyrano[3,2-b]pyridine-2-carboxylate.

8. A compound according to claim 1 which is 8-chloro-4,10-dihydro-4,10-dioxo-1H-1-benzopyrano[3,2-b]pyridine-2-carboxylic acid.

9. A compound according to claim 1 which is 4,10-dihydro-4,10-dioxo-1H-1-benzopyrano[3,2-b]pyridine-2-carboxylic acid.

10. A compound according to claim 1 which is 7-methoxy-4,10-dihydro-4,10-dioxo-1H-1-benzopyrano[3,2-b]pyridine-2-carboxylic acid.

11. A compound according to claim 1 which is 1-methyl-8-chloro-4,10-dihydro-4,10-dioxo-1H-1-benzopyrano[3,2-b]pyridine-2-carboxylic acid.

12. A compound according to claim 1 which is 1-methyl-4,10-dihydro-4,10-dioxo-1H-1-benzopyrano[3,2-b]pyridine-2-carboxylic acid.

13. A compound according to claim 1 which is 1-n-propyl-8-chloro-4,10-dihydro-4,10-dioxo-1H-1-benzopyrano[3,2-b]pyridine-2-carboxylic acid.

14. A compound according to claim 1 which is 1-benzyl-8-chloro-4,10-dihydro-4,10-dioxo-1H-1-benzopyrano[3,2-b]pyridine-2-carboxylic acid.

* * * * *